US00RE40401E

(19) United States
(12) Reissued Patent
Dardik

(10) Patent Number: US RE40,401 E
(45) Date of Reissued Patent: Jun. 24, 2008

(54) THERAPEUTIC EXERCISE PROGRAM

(75) Inventor: Irving I. Dardik, Califom, NJ (US)

(73) Assignee: Lifewaves International, Inc., Califon, NJ (US)

(21) Appl. No.: 09/573,884

(22) Filed: May 17, 2000

Related U.S. Patent Documents

Reissue of:
(64) Patent No.: 5,752,521
Issued: May 19, 1998
Appl. No.: 08/151,508
Filed: Nov. 12, 1993

(51) Int. Cl.
*A61B 5/02* (2006.01)

(52) U.S. Cl. ..... 600/520; 482/9
(58) Field of Classification Search ..... 600/500–503; 482/8–9
See application file for complete search history.

(56) References Cited

U.S. PATENT DOCUMENTS

| | | | | |
|---|---|---|---|---|
| 3,518,985 | A | 7/1970 | Quinton | 128/707 |
| 3,675,640 | A | 7/1972 | Gatts | 272/DIG. 6 |
| 3,802,698 | A | 4/1974 | Burian et al. | 272/57 R |
| 3,978,849 | A | 9/1976 | Geneen | 128/2.05 T |
| 4,278,095 | A | 7/1981 | Lapeyre | 128/689 |
| 4,301,808 | A | 11/1981 | Taus | 128/687 |

(Continued)

FOREIGN PATENT DOCUMENTS

| | | |
|---|---|---|
| CA | 2091101 | 9/1993 |
| CN | 1095917 | 12/1994 |
| DE | 3045923 | 9/1981 |
| DE | 3409792 | 9/1984 |
| DE | 3532620 | 3/1986 |

(Continued)

OTHER PUBLICATIONS

Acker J.E., Jr. et al., "Assessing psychlogical problems from a cardiologist's point of view," (Abstract) *Advances in Cardiology*31 at 218–22 (1982).
Ades P.A. et al., "Hypertension, exercise and beta–adrenergic blockade," (Abstract) *Annals of Internal Medicine*, 109 (8) at 629–34 (Oct. 15, 1988).
Aizaki T. et al., "Development of an ambulatory 24–hour recording device of electrocardiogram and exercise intensity and its analytic system," (Abstract) *Japan Journal of Med. Electron. Biol. Eng.* 32/2 at 83–90 (1994).

(Continued)

*Primary Examiner*—John P. Lacyk
(74) *Attorney, Agent, or Firm*—Greenberg Traurig, LLP; Paul F. McQuade

(57) ABSTRACT

A therapeutic exercise program for treating a patient whose abnormal condition, regardless of its nature and origin, is indicated by a resting heart pulse rate that deviates from the normal resting rate and a maximum heart pulse rate obtainable by physical exertion that deviates from the normal maximum rate, i.e., compromised range and flexibility. At the outset of the program, the patient is tested to determine his initial heart pulse range extending between his resting and maximum heart pulse rates to provide a base line for the program. In the course of the program, the patient whose heart beat is continuously monitored while exercising, undergoes a series of exercise-relaxation cycles. During each cycle, the exercising patient expends a surge of energy giving rise to a high pulse peak rate, the patient then relaxing to complete the cycle. This energy surge induces in the patient's heart a pendulum effect, causing the pulse rate to swing down from the peak rate to a resting rate below that in the initial range. The temporal conditions under which the program is conducted and its duration are such as to bring about a progressive rise in the maximum pulse rate attainable by the patient and to expand his range and increase the flexibility whereby at the conclusion of the program, the patient's maximum heart pulse rate and resting pulse rate approach those of an individual free of the abnormal condition.

21 Claims, 1 Drawing Sheet

U.S. PATENT DOCUMENTS

| | | | | |
|---|---|---|---|---|
| 4,358,105 | A | 11/1982 | Sweeney, Jr. | 272/73 |
| 4,367,752 | A | 1/1983 | Jimenez et al. | 128/689 |
| 4,425,921 | A | 1/1984 | Fujisaki et al. | 128/690 |
| 4,436,097 | A | 3/1984 | Cunningham | 128/707 |
| 4,566,456 | A | 1/1986 | Koning et al. | 128/419 |
| 4,613,129 | A | 9/1986 | Schroeder et al. | 272/73 |
| 4,622,980 | A | 11/1986 | Kunig | 128/704 |
| 4,683,891 | A | 8/1987 | Cornellier et al. | 128/630 |
| 4,719,920 | A | 1/1988 | Alt et al. | 128/419 |
| 4,788,983 | A | 12/1988 | Brink et al. | 128/734 |
| 4,807,639 | A | 2/1989 | Shimizu et al. | 128/690 |
| 4,867,442 | A | 9/1989 | Matthews | 272/93 |
| 4,883,063 | A | 11/1989 | Bernard et al. | 128/670 |
| 4,896,675 | A | 1/1990 | Ohsuga et al. | 128/671 |
| 4,938,228 | A | 7/1990 | Righter et al. | 128/690 |
| 5,007,430 | A | 4/1991 | Dardik | 128/696 |
| 5,163,439 | A | 11/1992 | Dardik | 128/696 |
| 5,267,568 | A | 12/1993 | Takara | 128/687 |
| 5,410,472 | A | 4/1995 | Anderson | 364/413.04 |
| 6,662,032 | B1 | 12/2003 | Gavish et al. | 600/323 |

FOREIGN PATENT DOCUMENTS

| | | |
|---|---|---|
| DE | 4338958 | 5/1994 |
| EP | 5949 | 12/1979 |
| EP | 117330 | 9/1984 |
| EP | 172747 | 2/1986 |
| EP | 181067 | 5/1986 |
| EP | 419103 | 3/1991 |
| EP | 556702 | 8/1993 |
| FI | 8304152 | 5/1985 |
| FI | 8900776 | 8/1989 |
| FR | 2569158 | 2/1986 |
| FR | 2599616 | 12/1987 |
| GB | 2052051 | 1/1981 |
| GB | 2165352 | 4/1986 |
| GB | 2184361 | 6/1987 |
| GB | 2253706 | 9/1992 |
| GB | 2306659 | 5/1997 |
| WO | 85/00279 | 1/1985 |
| WO | 90/12538 | 11/1990 |
| WO | 93/14807 | 8/1993 |
| WO | 94/02904 | 2/1994 |

OTHER PUBLICATIONS

Brusis O.A., "Rehabilitating coronary patients through exercise," (Abstract) *Postgraduate Medicine*, 44 (1) at p. 131–5 (Jul. 1968).

Bryniarski L. et al., "Effect of exercise rehabilitation on heart rate variability in hypertensives after myocardial infarction," (Abstract) *Journal of Hypertension*, 15(12 pt 2) at 1739–43 (Dec. 1997).

Calzolari A.M. et al., "Rehabilitation of children after total correction of tetralogy of Fallot," (Abstract) *International Journal of Cardiology*, 28 (2) at 151–8 (Aug. 1990).

Cerny F.J., "Relative effects of bronchial drainage and exercise for in–hospital care of patients with cystic fibrosis," (Abstract) *Phys. Ther.*69/8 at 633–639 (1989).

Claus J. et al., "Special aspects of physical training during the rehabilitation stage of coronary patients," (Abstract) *Herz,*16 (4) at 199–209 (Aug. 1991).

Cooney M.M. et al., "Hydraulic resistance exercise benefits cardiovascular fitness of spinal cord injured," (Abstract) *Medicine and Science in Sports and Exercise,* 18 (5) at 522–5 (Oct. 1986).

Crakes J.G. et al., "Endpoints of chronobiologic cardiovascular monitoring during pregnancy for planning exercise and assessing effects," (Abstract) *Progress in Clinical and Biological Research*, 341A at 605–14 Ref: 28 (1990).

Dardik Irving I., "Research proposals for studying mind–body interactions, Cardiocybernetics* :Relaxation through Exercise, " *Advances, Journal of Institute for the the Advancement of Health*, vol. 8, No. 3 at 56–59 (Summer 1986).

De Vries H.A. et al., "Electromyographic comparison of single doses of execise and meprobamate as to effects on muscular relaxation," (Abstract) *American Journal of Physical Medicine*, 51 (3) at 130–41 (Jun. 1972).

DiCarlo S. et al., "Hemodynamic and energy cost responses to changes in arm exercise technique," (Abstract) *Physical Therapy*, 63 (10) at 1585–92 (Oct. 1983).

Estok P.J. et al., "Jogging: cardiovascular benefits and risks," (Abstract) *Nurse Pratictioner,* 11 (5) at 21–8 (May 1986).

Ewart C.K. et al. "Usefulness of self–efficacy in predicting overexertion during programmed exercise in coronary artery disease," (Abstract) *American Journal of Cardiology*, 57 (8) at 557–61 (Mar. 1, 1986).

Fletcher G.F., "Rehabilitative exercise for the cardiac patient. Early phase," (Abstract) *Cardiology Clinics*, 11 (2) at 267–75 Ref: 20 (May 1993).

Fletcher G.F. et al., "Continuous ambulatory electrocardiographic monitoring. Use in cardiac exercise programs," (Abstract) *Chest*, 71 (1) at 27–32 (Jan. 1977).

Freedman R. et al., "Biofeedback and progressive relaxation treatment of sleep–onset insomnia: a controlloed, all–night investigation," (Abstract) *Biofeedback and Self Regulation*, 1 (3) at 253–71 Journal code: A15 (Sep. 1976).

Fujita Y. et al., "Relationship between age–adjusted heart rate and anaerobic threshold in estimating exercise intensity in diabetics," (Abstract) *Diabetes Res. Clin. Pract.*, 8/1 at 69–74 (1990).

Garfinkel Alan et al., "Heart Rate Dynamics After Acute Cocaine Administration," *Journal of Cardiovascular Pharmacology*, vol. 19, No. 3 at 453–459 (1992).

Goldberg A.P. et al., "Therapeutic benefits of exercise training for hemodialysis patients," (Abstract) *Kidney International Supplement*, 16 at S303–9 (Dec. 1983).

Gordon N.F. et al., "Exercise and mild essential hypertension," (Abstract) *Primary Care; Clinics in Office Practice*, 18 (3) at 683–94 Ref: 60 (Sep. 1991).

Greer M. et al., "Physiological responses to low–intensity cardiac rehabilitation exercises," (Abstract) *Physical Therapy*, 60 (9) at 1146–51 (Sep. 1980).

Hertzeanu H.L. et al., "Ventricular arrhythmias in rehabilitated and nonrehabilitated post–myocardial infarction patients with left ventricular dysfunction," (Abstract) *American Journal of Cardiology*, 71 (1) at 24–7 (Jan. 1, 1993).

Hooker S.P. et al., "Physiologic effects of electrical stimulation leg cycle exercise training in spinal cord injured persons, " (Abstract) *Archives of Physical Medicine and Rehabilitation*, 73 (5) at 470–6 (May 1992).

Iwadare M. et al., "Exercise prescription for physical training in hypertensive patients," (Abstract) *Nippon Rinsho. Japanese Journal of Clinical Medicine*, 50 Suppl. at 160–7 (May 1992).

Jovanovic–Peterson L. et al., "Randomized trial of diet versus diet plus cardiovascular conditioning on glucose levels in gestational diabetes," (Abstract) *American Journal of Obstetrics and Gynecology,* 161 (2) at 415–9 (Aug. 1989).

Katoh J. et al., "Cardiorespiratory effects of weight reduction by exercise in middle–aged women with obesity," (Abstract) *Journal of International Medical Research*, 22 (3) at 160–4 (May–Jun. 1994).
Kellermann J.J., "Rationale of exercise therapy in patients with angina pectoris with normal and impaired ventricular function," (Abstract) *Chest. 101/5 Suppl.*, at 322S–325S (1992).
Kohno M. et al., "Effects of exercise therapy on blood pressure and hormonal factors in subjects with borderline and mild hypertension," (Abstract) Bull. Phys. Fitness Res. Inst. –/72 at 81–86 (1989).
Malikov V.A. et al., "Selection of optimal training exercise and training schedule for patients with ischemic heart disease at the early periods after aortocoronary bypass," (Abstract) *Kardiologiia* 31 (7) at 17–20 (Jul. 1991).
Malpas et al., "Circadian Variation Of Heart Rate Variability," Cardiovascular Research, vol. 24, at 210–213 (1990).
Maynard T., "Exercise: Part II. Translating the exercise prescription," (Abstract) *Diabetes Educator*17 (5) at 384–95 Ref: 13 (Sep. –Oct. 1991).
Mead W.F., "Exercise rehabilitation after myocardial infarction," (Abstract) *American Family Physician*, 15 (3) at 121–5 Mar. 1977).
Meyer K. et al., "Resistance exercise in comparison to bicycle ergometry. A study into the suitability of resistance training in exercise therapy for coronary patients," (Abstract) *Z. Kardiol.*, 81/10 at 531–537 (1992).
Meyer K. et al., "Can the training of coronary patients be monitored by readily measurable parameters?," (Abstract) *Herz.*, 16 (4) at 251–6 (Aug. 1991).
Mink B.D., "Pulmonary concerns and the exercise prescription," (Abstract) *Clinics in Sports Medicine,* 10 (1) at 105–16 Ref: 33 (Jan. 1991).
Neubauer B. et al., "Analysis of heart rate variations in patients with multiple sclerosis," *Journal of Neurology, Neurosurgery, and Psychiatry,* 41 at 417–419 (1978).
Oldridge N.B., "Carotid palpation, coronary heart disease and exercise rehabilitation," (Abstract) *Medicine and Science in Sports and Exercise*, 13 (1) at 6–8 (1981).
Ramazanoglu Y.M. et al., "Cardiorespiratory response to physical conditioning in children with bronchial asthma," (Abstract) *Pediatric Pulmonology*, 1 (5) at 272–7 (Sep.–Oct. 1985).
Reilly K. et al., "Differences between a supervised and independent strength and conditioning program with chronic low back syndromes," (Abstract) *Journal of Occupational Medicine,* 31 (6) at 547–50 (Jun. 1989).
Samitz G., "Aerobic upper body exercise. An unused potential in exercise therapy," (Abstract) *Wien. Med. Wochenschr.*, 142/14 at 309–313 (1992).
Schechtman V.L., "Dynamic Analysis of Cardiac R–R Intervals in Normal Infants Who Subsequently Succumbed to the Sudden Infant Death Syndrome," *Pediatric Research*, vol. 31, No. 6 at 606–612 (1992).
Schwartz Tony, "Making Waves. Can Dr. Irv Dardik's Radical Exercise Therapy Really Work Miracles," *New York* at 31–39 (Mar. 18, 1991).
Sparks K.E. et al. , "Alternatives for cardiac rehabilitation patients unable to return to a hospital–based program," (Abstract) Heart and Lung , 22 (4) at 298–303 (Jul.–Aug. 1993).
Stephens R. et al., "Effects of self–monitored exercise on selected blood chemistry parameters of end–stage renal disease patients," (Abstract) *American Journal of Physical Medicine and Rehabilitation*, 70 (3) at 149–53 (Jun. 1991).
Stevens R. et al., "Comparison of supervised and unsupervised exercise training after coronary bypass surgery," (Abstract) *American Journal of Cardiology*, 53 (11) at 1524–8 (Jun. 1, 1984).
Tamiya N., "Study of physical fitness in children, and its application to pediatric clinics and sports medicine," (Abstract) *Hokkaido Igaku Zasshi. Hokkaido Journal of Medical Science*, 66 (6) at 849–67 (Nov. 1991).
Taniguchi K. et al., "Predischarge early exercise therapy in patients with acute myocardial infarction on the basis of anaerobic threshold (AT)," (Abstract) *Jpn. Circ. J.*, 54/11 at 1419–1425 (1990).
Todd I.C. et al., "Effect of exercise training on the total ischaemic burden: an assessment by 24 hour ambulatory electrocardiographic monitoring," (Abstract) *British Heart Journal*, 68 (6) at 560–6 (Dec. 1992).
Ueshima K. et al., "Management and evaluation of non–supervised home exercise program in a convalescent phase of acute myocardial infarction," (Abstract) *Japanese Circulation Journal*, 54 (11) at 1437–42 (Nov. 1990).
van Dixhoorn J. et al., "Physical training and relaxation therapy in cardiac rehabilitation assessed through a composite criterion for training outcome," (Abstract) *American Heart Journal*, 118(3) at page 545–52 (Sep. 1989).
Waddington J.L. et al., "Resting heartrate variability in man declines with age," *Experience*, 35 at 1197–1198 (1979).
Wheeler Timothy et al., "Cardiac Denervation in Diabetes," *British Medical Journal*, 4 at p. 584–586 (Dec. 8, 1973).
Williams L.R. et al., "Vascular rehabilitation: benefits of a structured exercise/risk modification program," (Abstract) *Journal of Vascular Surgery*, 14 (3) at 320–6 (Sep. 1991).
Williams M.A. et al., "Guidelines for exercise therapy of the elderly after myocardial infarction," (Abstract) *Eur. Heart J. 5, Supplement E*at 121–123 (1984).
Wolfe L.A. et al., "Prescription of aerobic exercise during pregnacy," (Abstract) *Sports Medicine*, 8 (5) at 273–301 Ref: 133 (Nov. 1989).

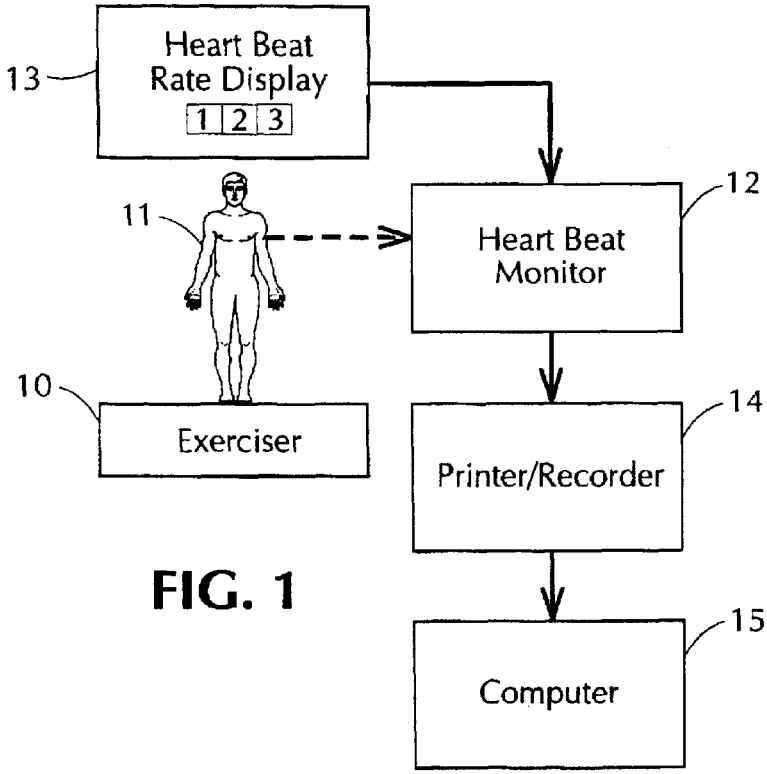
FIG. 1
FIG. 2
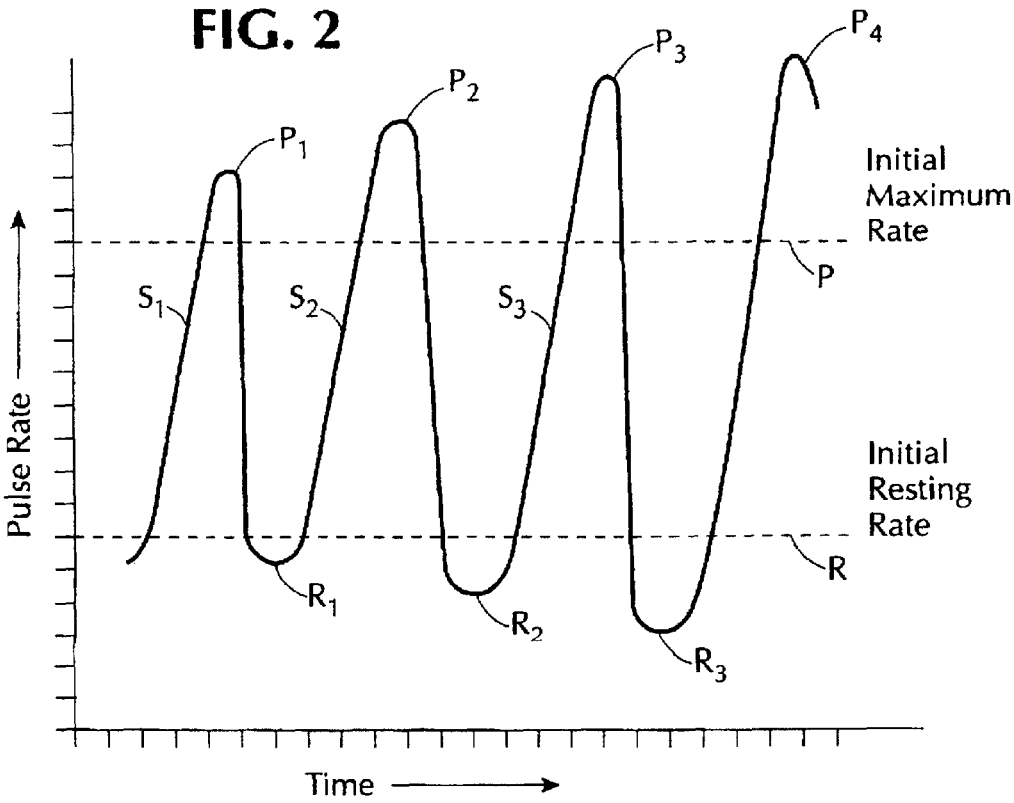

THERAPEUTIC EXERCISE PROGRAM

Matter enclosed in heavy brackets [ ] appears in the original patent but forms no part of this reissue specification; matter printed in italics indicates the additions made by reissue.

*This application is a reissue application of U.S. patent application Ser. No. 08/151,508, filed Nov. 12, 1993, which issued as U.S. Pat. No. 5,752,521 on May 19, 1998, and which is hereby incorporated-by-reference herein in its entirety; and U.S. patent application Ser. No. 10/723,920 was filed on Nov. 25, 2003 as a continuation of this application as an additional reissue application of U.S. patent application Ser. No. 08/151,508.*

BACKGROUND OF THE INVENTION

1. Field of Invention

This invention relates generally to therapeutic exercise techniques, and more particularly to a therapeutic exercise program in which a patient having an abnormal condition undergoes a series of exercise-relaxation cycles in the course of which the patient's heart wave is modulated to improve his condition.

2. Status of Prior Art

The human heart consists of two pumps having similar outputs, one pump sending blood through a pulmonary network, the other through the systemic network of the body. The human heart pumps the entire blood contents of the body through its chambers every minute. In mechanical terms, the heart exerts between 35–50 foot-pounds of pressure every minute. During strenuous exercise, it may exert as much as 500 foot-pounds.

A heart beat or pulse is one complete pulsation of the heart. A typical infant has a heart rate at rest of 130 beats per minute. This rate thereafter slows down so that in adulthood the rate at rest is about 70 beats per minute. When an increased demand is made upon the heart, the heart pulse rate quickens and the heart also pumps more blood with each beat, so that the heart output can be nearly doubled from its normal resting output.

Physical activity requires the expenditure of energy, and with exercise the heart pulse rate of a child may rise as high as 200 beats per minute, the rate dropping to about 80 when the child lies down. With aging one experiences a progressive decline in the maximum heart pulse rate. In exercise physiology, the rule of thumb is that an individual's maximum heart rate is 220 minus his age. Hence for a 50 year old individual, his attainable maximum pulse rate is 220−50 which is 170 beats per minute.

My prior U.S. Pat. No. 5,007,430 discloses an exercise technique for inducing relaxation to counteract the adverse physiological and psychological effects of chronic stress on an individual. In this technique the individual being treated is coupled to a heart beat monitor and his heart beat is constantly monitored and displayed to him as he goes through a conditioning exercise session constituted by successive exercise-relaxation cycles running for a predetermined period.

In the course of each cycle, the individual while operating a stationary bicycle, a rowing machine or other exercise apparatus, is required to raise his level of exertion, as indicated by his perceived heart pulse rate, to a peak representing a predetermined safe upper limit, following which he is must decrease his exertion until he reaches a lower limit at which a recovery-relaxation response takes place. The upper and lower limits are determined by the individual's existing capacity for exercise and defines his target heart rate zone.

My prior exercise technique whose purpose is to relieve mental stress is grounded on the premise that the exertion experienced in exercise and the recovery therefrom entail physiological and psychological processes that effectively corresponding to stress and relaxation.

The present state of medical knowledge with regard to chronic diseases is such that no single cause or cure therefor has yet to be found. Chronic diseases have been imputed to a multitude of factors such as structural abnormalities, gene mutation and altered levels of chemicals, e.g. chloresterol, calcium, T-4 cells, etc. This is the current basis for biochemical testing of a patient's condition. Behavioral factors also come into play in producing such disorders as obesity, clinical depression and sleep abnormalities. Also taken into account in the etiology of diseases are environmental factors including pesticides, exposure to high voltage power lines and atmospheric pollution.

The current practice in treating patients who suffer from abnormal organic conditions involve the use of drugs, radiotherapy and surgical intervention, biofeedback and stress reduction being used to treat behavioral abnormalities.

The concern of the present invention is with treating patients having an abnormal condition which regardless of its cause and nature, is indicated by a depressed heart state, characterized by a resting heart rate that deviates from the normal resting rate and a maximum heart rate that deviates from the normal maximum rate. I have found that patients who suffer from various diseases, clinical depression, anorexia, and a host of other abnormalities, all exhibit a depressed heart condition. The extent to which the heart is depressed and impairs the patient's health varies from patient to patient. But it is this common denominator that is the foundation for an exercise program in accordance with the invention, whose objective is to lift this depression and restore the well being of the patient.

SUMMARY OF INVENTION

In view of the foregoing, the main object of this invention is to provide a therapeutic exercise program which subjects a patient having an abnormal condition to a series of exercise-relaxation cycles that serve to modulate this heart wave so that at the conclusion of the program the patient is to a substantial degree relieved of his abnormal condition.

A significant feature of the invention is that the exercise program is addressed to the common denominator of abnormality regardless of its cause and nature, this being a depressed heart state characterized by a resting pulse rate that deviates from the normal resting rate and a maximum pulse rate that deviates from a normal maximum rate. The treatment of the patient is directed toward the return of the heart condition to a normal state, involving no drugs, radiotherapy, genes or any other known form of medical treatment or intervention, and which if conducted properly within a given patient's exercise capability, is free of adverse effects.

More specifically, an object of the invention is to provide a therapeutic exercise program to prevent, reverse or cure auto-immune, cardiovascular and other diseases as well as behavioral disorders regardless of the initial inciting agent therefor.

Briefly stated, these objects are obtained by a therapeutic exercise program for treating a patient whose abnormal condition, regardless of its nature and origin, is indicated by a resting heart pulse rate that deviates from the normal resting rate and a maximum heart pulse rate obtainable by physical exertion that deviates from the normal maximum rate. At the outset of the program, the patient is tested to determine his initial heart pulse range extending between his resting and maximum heart pulse rates to provide a base line for the program. In the course of the program, the patient whose heart beat is continuously monitored while exercising or operating an exercise machine, undergoes a series of exercise-relaxation cycles.

During each cycle, the exercising patient expends a surge of energy giving rise to a high pulse peak rate, the patient then relaxing to complete the cycle. This energy surge induces in the patient's heart a pendulum effect, causing the pulse rate to swing down from the peak rate to a resting rate below that in the initial range. The temporal conditions under which the program is conducted and its duration are such as to bring about a progressive rise in the maximum pulse rate attainable by the patient and to expand his range whereby at the conclusion of the program, the patient's maximum heart pulse rate and resting pulse rate approach those of an individual free of the abnormal condition.

BRIEF DESCRIPTION OF DRAWINGS

For a better understanding of the invention as well as other object and features thereof, reference is made to the following detailed description to be read in conjunction with the annexed drawings wherein:

FIG. 1 is a block diagram of a system for carrying out a therapeutic exercise program in accordance with the invention; and FIG. 2 illustrates the heart wave of a patient undergoing a series of exercise-relaxation cycles in accordance with the program.

DETAILED DESCRIPTION OF INVENTION

Wave Theory:

The theory underlying my invention is that the interactions which take place in the human organism and involve the biochemistry of the organism and the behavior of its organs is based upon wave communication, not on the complexity of the structure itself.

In my invention we do not deal with multi-factorial structural phenomena from the bottom up and linear levels of measurement, for the invention is concerned with the use and shaping of wave activity as the ultimate cause and as a means to alleviate or cure organic and psychological disorders from the top down.

The present invention exploits the organization of individual behavior at the macro level, monitored and manipulated through the single concept of a heart wave to modulate and direct the behavioral wave patterns of many complex biochemical phenomena at the micro level. The invention recognizes that all forms of behavior are in fact wave behaviors. For example, the human organism has cycles or waves of behavior which expend energy and recover energy. The same is true for emotional stress and emotional recovery which is a wave of energy. This also applies to being awake or being asleep; or not eating and eating. All of these behaviors are waves of energy flux. The same concept of wave energy flux is true for all organ systems of the body and is especially obvious with the heart rate which is currently measured as an average linear rate over time. However, I have discovered this to be not a heart rate but a heart wave in which each heart beat entails a contraction/systole and relaxation/diastole which rises and falls over time to create wave motion of the heart beat. This I find to be a heart wave of energy flux. The heart wave is unique in that it represents the connection and the window between the different behavioral waves of the organism and its relationship to the environmental waves such as day/night cycles, climate cycles, etc., connecting these to the internal environment of molecular biological cellular/chemical/genetic oscillations, all manifesting behavioral waves of energy expenditure and recovery.

This present invention is based on the recognition that the waves produced by the heart are related not only to the behavioral waves of the human organisms which are cyclic in nature but also to molecular biological waves. All organ systems oscillate, and the heart produces a heart wave. All cells and genes undergo oscillation so that molecule biology is also a form of wave activity.

Wave activity occurs at the following hierarchical levels:

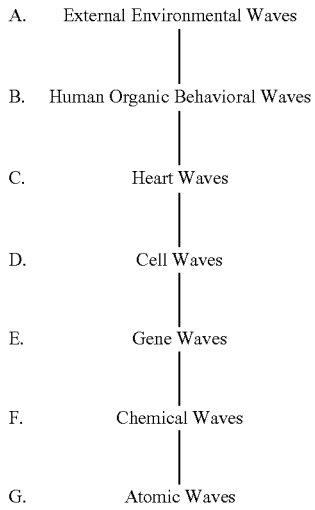

All of the above forms of wave activity occur simultaneously within and across hierarchical levels. Any disorder at the biochemical level will therefore reflect changes in the heart wave and in the behavior of the patient, whether it be behavioral disorders or organic disorders. The waves therefore represent the common denominator of simultaneous, coherent communications throughout the organism which is responsible for health and organization.

Wave shape is the key factor responsible for the flexibility and simultaneous coherent organization of all the chemistry, cells and of the various organ systems responsible for health, performance and longevity. This is an "action at a distance" principle. From this perspective, all disease represents a disordered wave pattern in which the shape of the wave is distorted, giving rise to chemical imbalances where the timing is off and out of sync. The cure for diseases therefore is to correct, i.e., reshape the wave disorder by overriding or ablating the abnormal wave pattern, using the heart wave as the means to analyze and to bring into being over time, new heart wave patterns to reverse chronic disease or other abnormality.

I have discovered that the different cycles/waves of the different hierarchical levels of the human organism and its external environment are fractal shapes of one another. Fractal shaping means that communication is continuous and simultaneous across hierarchical levels. The fractal wave pattern shape is what determines the health versus chronic disease of the organism.

The present invention uses the heart wave as a means of diagnosing, monitoring and modulating to recreate normal wave patterns of the 24-hour cycle, which is then used to create the appropriate monthly/lunar cycle, which is then used to create the yearly cycle and ultimately the lifetime cycle. It is not a matter of merely making or creating waves, for the actual shape of the wave is critical in terms of its flux from crest to trough, i.e., amplitude and rate of change, i.e., acceleration and rate of recovery/deceleration.

The objective is to enhance the master heart wave reactivity and flexibility, its range/amplitude by appropriately integrating behavioral heart wave patterns monitored and analyzed by a computer. As the heart wave patterns are developed and changed over time toward normalcy, simultaneously the enormous complexity of biochemical interactions becomes more coherent to reverse the chronic diseases or other abnormality.

All wave behaviors including exercise and recovery, wakefulness and sleep, diet and eating, emotional arousal and relaxation, etc., are coherently organized to create the appropriate heart wave patterns. In particular, exercise and recovery are most important because of the ease and occurring with which one can create the cycles of energy expenditure and recovery.

The shape of the wave is novel and different from current patterns of behavioral approaches, i.e., relaxation meditative techniques, aerobics, interval training, diets, all of which use prolonged linear behavioral approaches. In contrast, the novel exercise technique I am using focuses in large measure on the spiking of wave patterns, i.e., short bursts of energy expenditure and recovery designed to increase the flexibility and range of heart waves. This is consistent with the examples hereafter given.

Spiking means the rate of acceleration and deceleration in the amplitude of the wave. The spiking waves are then developed into fractal patterns of sets of cycles, series of cycles within a 24-hour period, and thereby fractally shaped into the 24-hour cycle pattern. This is then fractally shaped into the lunar monthly cycle, which is then fractally shaped into the yearly cycle, and is then fractally shaped into the life cycle. All of this is computer monitored so that the fractals can be analyzed for diagnostic and therapeutic purposes.

Examples of Wave Activity

1. The day/night cycle of the environment at the equator is sharply defined with minimal dawn and minimal dusk, i.e., a spike. It is known that chronic diseases, in particular depression, multiple sclerosis and more recently, as described in Newsweek, Jun. 7, 1993, on a report from the University of California, that cancers of the colon, prostate and breast are "virtually unknown" at the equator, and that with each rise in latitude, these diseases increase in incidence. I have found this to be so because the day/night wave pattern becomes more linear, e.g. more dark/less light until one reaches the extreme northern or southern latitudes with virtually six months dark and six months light.

2. Children have extremely high heart rates up to 200 or more with exercise and when they lie down, the heart rates then drops to the 80s. As we get older, it is known that our maximum heart rate drops progressively. I have found that the pattern of heart rates drops which are experienced with chronic diseases are indicative of these diseases.

3. Labor contractions at birth are cyclic. Work done at the Karolinska Institute in Sweden has shown that the cyclic contractions of the skull and brain of a baby when they are born results in enormous outputs of various hormones, including adrenalin, etc., (with levels which only occur in later life with extreme exercise). These labor contractions were found to be responsible for enhanced immune system, cardiovascular and respiratory functions, neurophysiological behavior, etc.

4. The hunting of animals in the wild is cyclic in nature, reflecting the spike to which I have referred. Animals in the wild rarely have chronic diseases. However, when placed in zoos or domesticated, the wave patterns are flattened and become less responsive, and the incidences of chronic diseases then rival those of humans. It is also now generally recognized that chronic diseases and behavioral disorders such as asthma, suicide, depression, drug addiction, criminal behavior and cancer are dramatically on the rise.

The Invention:

In a therapeutic exercise program in accordance with my invention, the program is tailored to treat a patient having an abnormal condition. This condition, regardless of its cause and nature, is indicated by a depressed heart state characterized by a resting heart pulse rate that deviates from the normal resting rate and a maximum pulse rate obtained by physical exertion that deviates from the normal maximum rate.

At the outset of the program, the patient is tested to determine the initial heart pulse range extending between his resting and maximum heart pulse rates to provide a base line for the program. This initial range varies from patient to patient. Thus one patient may show an initial range whose maximum heart rate is 107 and whose resting heart rate is 51, while another may show an initial range going from 130 down to 100. In both instances, the range is narrow and the heart is in a depressed state.

The purpose of the exercise program is to expand the range and flexibility and in doing so to relieve the patient of his or her abnormal condition.

FIG. 1 shows in block diagram the basic elements of a system for carrying out a program in accordance with the invention; the system including an exercise machine 10. This machine may be a stationary bicycle, a rowing machine or an other form of exercising apparatus suitable for a patient 11 having an abnormal condition. In practice, in lieu of an exercise machine, the patient may exercise by walking, running or jumping, or simply by arm and shoulder movements.

When machine 10 is operated by patient 11 who exerts himself, the heart beat of the patient rises as a function of this exertion. Patient 11 is provided with a heart beat detector of any commercially available type which is coupled magnetically or by wireless means to a heat beat monitor 12 whose reading is presented on an electronic display 13. This display which is of the digital type is so placed that it can be read by the patient and the supervisor of the program.

Heart beat monitor is coupled to a recorder 14 that graphically records and prints out the heart wave produced by the series of exercise-relaxation cycles the patient undergoes in the course of a session whose duration is controlled by the supervisor.

The output of recorder 14 is digitalized and applied to a digital computer 15 in which the recordings produced in successive exercise sessions are stored and diagnosed to afford an analyses of the progressive changes taking place in the patient's condition.

FIG. 2 graphically illustrates, in idealized form, the heart wave generated by the patient during successive exercise-relaxation cycles. The initial range of the patient, as determined at the outset of the program, is indicated in FIG. 2 by level P representing the maximum heart pulse rate the patient is able to then attain, and by level R representing his resting pulse rate. Because the patient suffers from an abnormal condition, regardless of its cause and nature, this initial range is the common denominator. Hence levels R and P are both deviate from normal, indicating a depressed heart state and a narrow heart wave range.

During each of the successive cycles, the patient operating the exercise machine or undergoing exercise is required to exert himself to produce a surge of energy giving rise to a rapid rise in pulse rate.

The first surge $S_1$ results in a maximum pulse rate $P_1$ that is somewhat above the initial maximum pulse rate line P. The patient, having attained peak $P_1$, then relaxes so that the pulse rate proceeds to drop sharply. But the pulse rate does not then drop to the initial resting level R, for the energy surge induces in the patient's heart a pendulum effect, causing the pulse rate to swing down to a resting rate $R_1$ which is below the initial resting rate level R.

A pendulum is a body suspended from a fixed support when is free to swing back and forth under the influence of gravity. The amplitude of the back and forth oscillation depends on the force of the actuating impulse which incites the pendulum into motion. If therefore at the end of an oscillation cycle, an impulse is applied causing the pendulum to swing forth to a greater degree than in the preceding cycle, it will then swing back to a greater degree.

We have found that the human heart behaves in a similar manner, and that a sudden surge of energy which causes the heart pulse rate to swing to a peak value, the down swing will cause the heart rate to fall below its initial resting rate.

The spiked wave created by surge $S_1$ and the return swing $R_2$ represents the amplitude envelope of the varying heart pulse rate, for each point in the wave form represents a is different pulse rate. Hence the envelope of the wave form reflects the varying repetition rates or frequencies of the heart beat.

In the next exercise-relaxation cycle, an energy surge $S_2$ produces a higher maximum pulse rate $P_2$ and a still lower resting rate $R_2$. And in the succeeding cycles produced by surges $S_3$ and $S_4$, still high maximum rates are produced. It is to be understood that from cycle to cycle, the peaks do not necessarily progressively increase, for a high peak may be succeeded by a lower peak.

Thus the successive exercise-relaxation cycles occurring in the course of an exercising session, act to expand the heart range of the patient. The temporal conditions under which the program is conducted (time of day, season, etc.) and its duration which may extend for several days, weeks or months, are such as to bring about a progressive increase in the maximum pulse rate attainable by the patient and so expand the heart wave range whereby at the conclusion of the program the patient's maximum heart pulse rate and his resting rate approach those of an individual free of the abnormal condition for which the patient was treated.

The cycles are best done at certain times of the day according to the body's healthy physiological rhythms. I have found that unlike current thinking where exercise is believed to raise the immediate resting heart rate, that in fact is heretofore unknown phenomenon occurs in which a sudden rise in energy expenditure to a high heart rate will result in a pendulum effect, in other words, a lowering of the resting heart rate.

Computer technology makes it possible to analyze and compute the effects of the program for purposes of diagnosis and to determine the degree to which the patient is being restored to a healthy state. It is also useful to monitor wave fluctuations in temperature, blood pressure, EEG, EMG etc. The heart wave patterns with chronic disorders is where the heart wave loses its responsivity and flexibility to rapidly reach high numbers and to rapidly recover. Thus with chronic disorders the heart wave assumes a relatively long wave length, a lower amplitude, a narrower range and decreased flexibility reflecting similar patterns of biochemical flux and similar behavioral patterns of a chronic, linear, repititive nature. As pointed out by Ilya Prigogene, Nobel Laureate, fluctuations in wave patterns which go toward equilibrium and homogeneity result in molecular incoherence no matter how well organized and structured the molecules themselves are.

Shaping the Heart Wave:

An increase in the range of the heart wave resulting from the Program simultaneously enhances its flexibility. Shaping of the individual heart wave is effected by using exercise-recovery cycles, also by incorporating other behavioral waves of wakefulness and sleep, not eating and eating, and mental arousal and relaxation. Other techniques may be included, such as hot and cold showers, acupuncture, hyperthermia, and sun cycles, all forms of wave energy.

The appropriate shaping of the heart wave using the above modalities makes possible optimal fractal shaping of the following rhythms which enables the patient to prevent and reverse disease:

a. the circadian rhythm/24 hour wave b. the lunar monthly wave c. the yearly cycle Chronic diseases are characterized by:

1. Decreased range (lowered maximum amplitude and lowered resting pulse. Though some patients' heart rates are hyper-reactive, they eventually lower to subnormal levels as the Program proceeds and then the Program acts to raise the amplitude and flexibility as previously described.)
2. Decreased flexibility of the heart wave, i.e., slow response to any stressful perturbation or sometimes a hyperactive response to stress.

When the heart wave is "trained" or modulated through the Program to have an increased range and be more responsive, i.e., increased flexibility with a greater rate of change of acceleration and deceleration, we are then able to use the heart wave to shape the 24 hour cycle, and the monthly and yearly wave cycles which powerfully and simultaneously shape more responsive and coherent biochemical and genetic behavioral waves, thereby preventing and curing chronic diseases. It is the abnormal wave patterns of organism behavior and biochemical and genetic behaviors that are responsible for chronic diseases. These are restored to normal with the Program.

Computer Analyses:

To exploit the underlying periodic components of the heart wave, one may use conventional digital signal processing (DSP) techniques for this purpose. The basis for these techniques lies in the solution of the Fourier Integral and its more prolific descendant, the Fast Fourier Transform (FFT).

Their applicability in heart wave analysis is as follows:

The first approach of interest is to uncover the natural, low and high frequency components present in the heart wave. Ideally, this should be done in the absence of any specifically prescribed regimen of cycles which would corrupt the basic nature of the "baseline." What is expected during this phase of analysis is a definite indication of natural periods on the order of minutes through days. The DSP technique employed for this measurement is commonly called "harmonic analysis." In harmonic analysis a fundamental (lowest) frequency is defined for a given data set, and higher frequency components are computed as real multiples of this fundamental. Note that phase as well as amplitude information is available.

The second approach to analysis involves treatment of specific pieces of the heart wave, specifically those pieces corresponding to commencement through cessation of cycles. These sections should be treated as discrete time signals, as opposed to continuous time signals. Analysis of this type of signal differs from harmonic analysis in that the signal is not considered (i.e., assumed to be zero) outside of the defined limits. This approach will yield the specific frequency component "finger print" of any individual's heart wave cycle performance.

Taken together, these two approaches present the best available top level view of what is happening within the bio-system under analysis. Furthermore, through the accumulation of data sets on an individual, the specific monthly, yearly, etc., periodicities can be evaluated and shaped. Using this information, the physician can intelligently prescribe series and groups of cycles which re-enforce natural frequency components, negate undesirable components, and generally re-align and re-calibrate the individual's wave energy profile.

Examples of Treatment:

1. A 59-year-old patient with leukemia. Initial maximum heart rate was 107, resting heart rate was 51. After 8 months of modulating heart wave cycles with the Program, his heart rate maximum was 163, recovering down to low 60s, during which time his white cell count has been progressively dropping as much as 57,000 in the course of 2½ weeks.
2. 24-year-old girl with anorexia. Maximum heart rate 150, resting heart rate in the mid to low 40s. After 5 months of the Program, her maximum heart rate reached 190 and her resting heart rate recovering to the 60s. Anorexia resolved 100%.
3. A 30-year-old woman with multiple sclerosis whose maximum heart rate at onset was 120, with resting heart rates in the 40s. After treatment, the maximum heart rate reached 168, recovering down to the mid 50s. All symptoms of multiple sclerosis have cleared. Patient was able to get married.
4. 28-year-old female with about an eight-year history of being HIV positive and active AIDS symptoms for about 1½ years, including severe diarrhea, severe depression and lethargy, weight loss of 20 pounds, monilia infections of the mouth, and total anergy of the immune system (no immune response with subdermal injections of candida) and facial rash. All symptoms disappeared between 1½ and 3 months of treatment, including the first immune response to candida injections in a year and a half. Heart wave patterns at onset ranged from 33 low heart rate to a hyperreactive maximum (which occasionally occurs as a "chaotic" response to stress) of 190, which during the Program her heart rates ranged to a maximum of 180 recovering into the mid 60s.
5. An 18-year-old male with a grade 3 to 4 malignant astrocytoma of the brain—6 to 7 months post-op was disoriented, sleeping 18 hours a day, short term memory deficit, etc. Heart range was maximum 120 recovering to 50s. After 2 years on the Program, the maximum was in the 170s down to the 60s and 70s, and after 3 years there has been no evidence of tumor recurrence.
6. A 55-year-old male with severe peripheral ischemia and neuropathy due to embolism in both legs. Post-amputation of left foot, became severely addicted to Percodan narcotics for pain control and was refractory to medical treatment for suicidal depression. Heart waves ranged from the 100 maximum, down to 45 resting. After about 10 months on the Program his heart rates were 160 maximum, recovering down to the 60s. The depression cleared on the Program, his drug addictions disappeared, pain was relieved approximately 90% and he was able to go back to work.
7. A 28-year-old female with severe inflammatory disease of the bowel (Ileitis). Had previous surgery, was first seen by me when she was partially obstructed on a liquid diet, severe arthritis, unable to wear shoes and walking with great difficulty, and she also had erythema nodosum (an inflammatory disease of the skin) which was refractory to medical treatment including cortisone. She was to be placed on immunosuppressive therapy and surgery was planned at Mt. Sinai Hospital in New York. After one week on the Program, the inflammation subsided dramatically in the legs and she began to eat solid foods. After 3 months, all symptoms disappeared except for intermittent obstruction based on the mechanical scarring of the small intestine. At surgery, the involved intestine was removed, she is doing extremely well. Her initial heart rates were a resting heart rate of 100 to 110, with extreme hyperreactivity on just standing to approximately 150. After the few months on the Program her resting heart rates were in the 60s with her maximum heart rate to 180.
8. A 65-year-old male with chronic viral hepatitis, whose initial heart rate maximum was 115 with recoveries down to the low 40s. After approximately one year on the program, his liver enzymes which were elevated returned close to normal. His depression, fatigue and weakness which made it difficult for him to leave his apartment, cleared and he was able to go back to skiing and playing tennis in a normal way. His heart rates ranged up to high 150s and recovered down to the 50s.
9. A 44-year-old male with severe chronic fatigue syndrome who was unable to work anymore. His heart rate range was 125 maximum, recovering down to the mid 40s. After 3 months on the Program his range is in the low 50s and maximum is 170. His chronic fatigue is about 80% improved and he has been able to return to work.

While there has been disclosed a therapeutic exercise program in accordance with the invention, many changes and modifications may be made thereon without departing from the spirit of the invention.

Thus while the invention has been described as a program to improve the condition of a patient having an abnormality reflected by a depressed heart state, individuals more or less free of abnormality may benefit from the program which will serve to enhance their mental and physical well-being and possibly prevent the occurrence of a chronic disease.

I claim:

1. A therapeutic exercise program for treating a patient having an abnormal condition indicated by a maximum heart pulse rate that deviates from a normal maximum rate and a resting heart pulse rate that deviates from a normal resting rate whereby the heart rate range is compromised, the program being carried out by the steps of:

A. continuously monitoring the heart pulse rate of the patient in the course of the program as the patient exercises;

B. subjecting the patient to a series of exercise-relaxation cycles in which in the course of each cycle the exercising patient expends a surge of energy causing his pulse rate to reach a peak value above said resting heart rate to a degree that depends on the patient's physical state, at which point the patient then relaxes and his heart rate because of a pendulum effect induced in the patient's heart, swings down from the peak value to a point below said resting heart rate to produce a spiked heart wave; and C. continuing the program until the patient's maximum heart pulse rate and resting heart pulse rate approach those of an individual having a normal heart rate range and free from the abnormal condition.

2. A program as set forth in claim 1, in which at the outset of the program the initial resting pulse rate and the initial maximum pulse rate are measured to determine the existing range and flexibility extending between these rates, the program then being conducted to expand this range and flexibility.

3. A program as set forth in claim 2, in which in each cycle the surge raises the peak value above the initial maximum pulse rate, and the swing produces a resting rate below the initial resting rate.

4. A program as set forth in claim 2, in which the program is conducted under temporal conditions and for a duration which brings about a progressive rise in the maximum pulse rate attainable by the patient and expands his range and flexibility.

5. A program as set forth in claim 1, in which the heart waves produced by the series of exercise-relaxation cycles are digitized and fed into a computer which analyzes these waves.

6. A program as set forth in claim 1, in which the abnormal condition is a chronic disease.

7. A program as set forth in claim 1, in which the abnormal condition is a behavioral disorder.

*8. A computer readable medium containing a therapeutic exercise program for treating a patient having an abnormal condition indicated by a maximum heart pulse rate that deviates from a normal maximum rate and a resting heart pulse rate that deviates from a normal resting rate whereby the heart rate range is compromised, the program comprising:*

*A. continuously monitoring the heart pulse rate of the patient in the course of the program as the patient exercises;*

*B. subjecting the patient to a series of exercise-relaxation cycles in which in the course of each cycle the exercising patient expends a surge of energy causing his pulse rate to reach a peak value above said resting heart rate to a degree that depends on the patient's physical state, at which point the patient then relaxes and his heart rate because of a pendulum effect induced in the patient's heart, swings down from the peak value to a point below said resting heart rate to produce a spiked heart wave; and*

*C. continuing the program until the patient's maximum heart pulse rate and resting heart pulse rate approach those of an individual having a normal heart rate range and free from the abnormal condition.*

*9. The computer readable medium of claim 8, wherein at the outset of the program the initial resting pulse rate and the initial maximum pulse rate are measured to determine the existing range and flexibility extending between these rates, the program then being conducted to expand this range and flexibility.*

*10. The computer readable medium of claim 9, in which in each cycle the surge raises the peak value above the initial maximum pulse rate, and the swing produces a resting rate below the initial resting rate.*

*11. The computer readable medium of claim 9, in which the program is conducted under temporal conditions and for a duration which brings about a progressive rise in the maximum pulse rate attainable by the patient and expands his range and flexibility.*

*12. The computer readable medium of claim 8, in which the heart waves produced by the series of exercise-relaxation cycles are digitized and fed into a computer which analyzes these waves.*

*13. The computer readable medium of claim 8, in which the abnormal condition is a chronic disease.*

*14. The computer readable medium of claim 8, in which the abnormal condition is a behavioral disorder.*

*15. A system for performing a therapeutic exercise program on a patient, wherein said program comprises a conditioning exercise session that itself comprises successive exercise-relaxation cycles, and wherein said patient has a heart pulse rate and an abnormal condition indicated by a maximum heart pulse rate that deviates from a normal maximum rate and a resting heart pulse rate that deviates from a normal resting rate whereby the heart rate range is compromised, said system comprising:*

*a heart beat monitor that monitors said heart pulse rate in the course of the program;*

*a heart beat rate display connected to said heart beat monitor, wherein said display displays said heart pulse rate during said program; and*

*a computer connected to at least said heart beat monitor programmed so that in the course of each cycle the exercising patient expends a surge of energy causing his pulse rate to reach a peak value above said resting heart rate to a degree that depends on the patient's physical state, at which point the patient then relaxes and his heart rate because of a pendulum effect induced in the patient's heart, swings down from the peak value to a point below said resting heart rate to produce a spiked heart wave, said program continuing until said maximum heart pulse rate and said resting heart pulse rate approach those of an individual having a normal heart rate range and free from the abnormal condition.*

*16. The system of claim 15, wherein at the outset of the program the initial resting pulse rate and the initial maximum pulse rate are measured to determine the existing range and flexibility extending between these rates, the program then being conducted to expand this range and flexibility.*

*17. The system of claim 16, in which in each cycle the surge raises the peak value above the initial maximum pulse rate, and the swing produces a resting rate below the initial resting rate.*

*18. The system of claim 16, in which the program is conducted under temporal conditions and for a duration which brings about a progressive rise in the maximum pulse rate attainable by the patient and expands his range and flexibility.*

*19. The system of claim 15, in which the heart waves produced by the series of exercise-relaxation cycles are digitized and fed into a computer which analyzes these waves.*

*20. The system of claim 15, in which the abnormal condition is a chronic disease.*

*21. The system of claim 15, in which the abnormal condition is a behavioral disorder.*

* * * * *